US005759778A

United States Patent [19]

Li et al.

[11] Patent Number: 5,759,778

[45] Date of Patent: *Jun. 2, 1998

[54] METHOD OF NUCLEIC ACID SEQUENCE SELECTION

[75] Inventors: Wu-Bo Li, N. Potomac; Christian E. Gruber, Frederick; Joel A. Jessee, Mt Airy; Jhy-Jhu Lin, Gaithersburg, all of Md.

[73] Assignee: Life Technologies, Inc., Rockville, Md.

[ * ] Notice: The term of this patent shall not extend beyond the expiration date of Pat. No. 5,500,356.

[21] Appl. No.: 525,140

[22] Filed: Sep. 8, 1995

Related U.S. Application Data

[63] Continuation of Ser. No. 103,769, Aug. 10, 1993, Pat. No. 5,500,356.

[51] Int. Cl.$^6$ .............................. C12Q 1/68; G01N 33/53
[52] U.S. Cl. ............................ 435/6; 435/7.1; 435/7.5; 435/172.3
[58] Field of Search ................... 435/91.1, 91.2, 435/172.3, 6, 7.1, 7.2, 7.5, 18; 536/24.3

[56] References Cited

U.S. PATENT DOCUMENTS

| | | | |
|---|---|---|---|
| 4,800,159 | 1/1989 | Mullis et al. | 435/172.3 |
| 4,888,274 | 12/1989 | Raddingi et al. | 435/6 |
| 5,484,702 | 1/1996 | Ludwig | 435/6 |

OTHER PUBLICATIONS

Pruitt (1988) Gene 66, 121–134.
Vandeyar et al. (1988) Gene 65, 129–133.
Welcher et al. (1986) Nucleic Acids R. J. 14, 1023–1044.
Rashtehian et al. (1992) Analyt. Biochem. 206, 91–97.
Lenin (1987) "Genes: Third Edition" pp. 358–359, John Wiley & Sons, N.Y.
Promega Protocols and Applications Guide, Second Edition, Mar. 1991, Especially pp. 124–132 and 199–211.
Kawasaki, E.S. 1990 In "PCR Protocols: A Guide to Methods and Applications", Academic Press, Inc. CH. 3 pp. 21–27.
Day; et al. 1991. Biochemical Journal. vol. 278 pp. 735–740.
Watson, et al. 1992. Recombinant DNA 2$^{nd}$ Edition. Scientific American Books. Especially p. 107.
Guesdon, J–L. 1992. J. of Immunol. Methods vol. 150: No. 1–2 pp. 33–49.
Rigas, B. et al., "Rapid Plasmid Library Screening Using RecA–Coated Biotinylated Probes," *Proc. Natl. Acad. Sci. (U.S.A.)* 83:9591–9595 (1986).
Takabatake, T. et al., "Use of Purine–Rich Oligonucleotides in Triplex–Mediated DNA Isolation and Generation of Unidirectional Deletions," *Nucleic Acid Res.* 20: 5853–5854 (1992).
Ito, T. et al., "Triplex Affinity Capture of a SIngle Copy Clone from a Yeast Genomic Library," *Nucleic Acids Res.* 20: 3524 (1992).
Ito, T. et al., "Sequence–Specific DNA Purification by Triplex Affinity Capture," *Proc. Natl. Acad. Sci. (U.S.A.)* 89: 495–498 (1992).

Fry, G. et al., "A New Approach to Template Purification for Sequencing Applications Using Paramagnetic Particles," *BioTechniques* 13:124–126, 128–131 (1992).
Rubenstein, J.L.R. et al., "Subtractive Hybridization System Using Single–Stranded Phagemids with Directional Inserts," *Nucleic Acids Res.* 18:4833–4842 (1990).
Weiland, I. et al., "A Method for Difference Cloning: Gene Amplification following Subtractive Hybridization," *Proc. Natl. Acad. Sci. (U.S.A.)* 87:2720–2724 (1990).
Duguid, J.R. et al., "Isolation of cDNAs of Scrapie–Modulated RNAs by Subtractive Hybridization of a cDNA Library," *Proc. Natl. Acad. Sci. (U.S.A.)* 85:5738–5742 (1988).
Cook, D. et al., "The Use of Subtractive Hybridization to Obtain a DNA Probe Specific for *Pseudomonas solanacearum* race 3," *Molec. Gen. Genet* 227:401–410 (1991).
Herfort, M.R. et al., "Simple and Efficient Subtractive Hybridization Screening," *BioTechniques* 11:598, 600–603 (1991).
Barr, F.G. et al., "Application of a Subtraction Hybridization Technique Involving Photoactivatable Biotin and Organic Extraction to Soluble Hybridization Analysis of Genomic DNA," *Anal. Biochem.* 186:369 (1990).
Timblin, C. et al., "Application of PCR Technology to Subtractive cDNA Cloning: Identification of Genes Expressed Specifically in Murine Plasmacytoma Cells," *Nucleic Acids Res.* 18:1587 (1990).
Porteus, M.H. et al., "Isolation and Characterization of a Library of cDNA Clones That Are Preferentially Expressed in the Embryonic Telencephalon," *Molec. Brain Res.* 1:1 (1991).
Scott–Craig, J.S. et al., "Isolation of *Bradyrhizobium japonicum* DNA Sequences that are Transcribed at High Levels in Bacteroids," *Molec. Gen. Genet.* 228:356–360 (1991).
Wang, Z. et al., "A Gene Expression System," *Proc. Natl. Acad. Sci. (U.S.A.)* 88:11505–11509 (1991).
Swaroop, A. et al., "A Simple and Efficient cDNA Library Subtraction Procedure: Isolation of Human Retina–Specific cDNA Clones," *Nucl. Acids Res.* 19:1954 (1991).
Garber, A.T. et al., "A Novel Subtractive Hybridization Screening Method Yields Psoriasis–Associated Dermal Fibroblast cDNA Clones," *Clin. Res.* 39:472A (1991).
Hara, E. et al., "Subtractive cDNA Cloning Using Oligo (dT) 30–latex and PCR: Isolation of cDNA Clones Specific to Undifferentiated Human Embryonal Carcinoma Cells," *Nucleic Acids Res.* 19:7097–7104 (1991).
LeBeau, M.C. et al., "PCR–Driven DNA–DNA Competitive Hybridization: A New Method for Sensitive Differential Cloning," *Nucleic Acids Res.* 19:4778 (1991).
Sive, H.L. et al., "A Simple Subtractive Hybridization Technique Employing Photoactivatable Biotin and Phenol Extraction," *Nucleic Acids Res.* 16:10937 (1988).

*Primary Examiner*—James Ketter
*Assistant Examiner*—Irem Yucel
*Attorney, Agent, or Firm*—Howrey & Simon; Jeffrey I. Auerbach, Esq.; Kevin W. McCabe

[57] ABSTRACT

The present invention provides a method for the rapid isolation and recovery of a desired target DNA or RNA molecules from a mixture or library containing such molecules. The method involves the use of biotinylated probes and enzymatic repair-cleavage to eliminate undesired library members from a sample.

44 Claims, 1 Drawing Sheet

METHOD OF NUCLEIC ACID SEQUENCE SELECTION

CROSS-REFERENCE TO RELATED APPLICATIONS

This application is a continuation of U.S. patent application Ser. No. 08/103,769 (filed Aug. 10, 1993 now U.S. Pat. No. 5,500,356).

FIELD OF THE INVENTION

The invention relates to an improved method for isolating and recovering target DNA or RNA molecules having a desired nucleotide sequence. Specifically, it relates to a method for the rapid isolation of specific nucleic acid target molecules.

BACKGROUND OF THE INVENTION

The ability to clone gene sequences has permitted inquiries into the structure and function of nucleic acids, and has resulted in an ability to express highly desired proteins, such as hormones, enzymes, receptors, antibodies, etc., in diverse hosts.

The most commonly used methods for cloning a gene sequence involve the in vitro use of site-specific restriction endonucleases, and ligases. In brief, these methods rely upon the capacity of the "restriction endonucleases" to cleave double-stranded DNA in a manner that produces termini whose structure (i.e. 3' overhang, 5' overhang, or blunt end) and sequence are both well defined. Any such DNA molecule can then be joined to a suitably cleaved vector molecule (i.e. a nucleic acid molecule, typically double-stranded DNA, having specialized sequences which permit it to be replicated in a suitable host cell) through the action of a DNA ligase. The gene sequence may then be duplicated indefinitely by propagating the vector in a suitable host. Methods for performing such manipulations are well-known (see, for example, Perbal, B. *A Practical Guide to Molecular Cloning*, John Wiley & Sons, NY, (1984), pp. 208–216; Maniatis, T., et al. (In: *Molecular Cloning. A Laboratory Manual*, Cold Spring Harbor Press, Cold Spring Harbor, N.Y. (1982); Old, R. W. et al., In: *Principles of Gene Manipulation*, 2nd Ed., University of California Press, Los Angeles, (1981), all herein incorporated by reference).

In some cases, a gene sequence of interest is so abundant in a source that it can be cloned directly without prior purification or enrichment. In most cases, however, the relative abundance of a desired target DNA molecule will require the use of ancillary screening techniques in order to identify the desired molecule and isolate it from other molecules of the source material.

A primary screening technique involves identifying the desired clone based upon its DNA sequence via hybridization with a complementary nucleic acid probe. In situ filter hybridization methods are particularly well known (see, Sambrook, J., et al., In: *Molecular Cloning. A Laboratory Manual*, 2nd Ed., Cold Spring Harbor Laboratory Press, Cold Spring Harbor, N.Y. (1989)). In such methods, bacteria are lysed on the surface of the membrane filter and then incubated in the presence of a detectably labelled nucleic acid molecule whose sequence is complementary to that of the desired sequence. If the extract contains the desired sequence, hybridization occurs and thereby binds the labelled molecule to the adsorbent surface. The detection of the label on the adsorbent surface reveals that the bacteria sampled contained the desired cloned sequence.

Although these screening methods are useful and reliable, they require labor-intensive and time consuming steps such as filter preparation and multiple rounds of filter hybridization and colony platings/phage infections. Generally, these procedures will screen up to $10^6$ colonies effectively, but may take weeks or months to yield the desired clone.

Recently, other approaches have been developed to isolate recombinant molecules which have eliminated the tedious filter-handling procedure. These approaches employ conventional hybridization technology coupled with chromatography or magnetic particle technology. Rigas, B. et al., for example, reported a method for isolating one plasmid species from a mixture of two plasmid species. In the disclosed method, circular double-stranded plasmid DNA is hybridized to a RecA protein-coated biotinylated probe to form a stable triple-stranded complex, which is then selectively bound to an agarose-streptavidin column (Rigas, B. et al., *Proc. Natl. Acad. Sci. (U.S.A.)* 83: 9591–9595 (1986)). The method thus permits the isolation of cloned double-stranded molecules without requiring any separation of the strands.

A DNA isolation method, termed "triplex affinity capture," has been described in which a specific double-stranded genomic DNA is hybridized to a biotinylated homopyrimidine oligonucleotide probe to form a "triplex complex," which can then be selectively bound to streptavidin-coated magnetic beads (Ito, T. et al., *Nucleic Acids Res.* 20: 3524 (1992); Ito, T. et al., *Proc. Natl. Acad. Sci. (U.S.A.)* 89: 495–498 (1992)). Takabatake, T. et al. have described a variation of this technique that employs a biotinylated purine-rich oligonucleotide probe to detect and recover the desired nucleic acid molecule (Takabatake, T. et al., *Nucleic Acid Res.* 20: 5853–5854 (1992)). A practical drawback with these particular approaches is that they are restricted to isolation of target DNA sequences containing homopurine-homopyrimidine tracts.

Fry, G. et al. discuss a method for sequencing isolated M13-LacZ phagemids (Fry, G. et al., *BioTechniques* 13:124–131 (1992)). In this method, a clone is selected and the phagemid DNA is permitted to hybridize to a biotinylated probe whose sequence is complementary to the phagemid's lacZ region. The biotinylated probe is attached to a streptavidin-coated paramagnetic bead. Since the DNA bound to the bead can be separated from unbound DNA, the method provides a means for separating the cloned sequence from the bacterial sequences that are inevitably present (Fry, G. et al., *BioTechniques* 13: 124–131 (1992)).

Still another method of screening recombinant nucleic acid molecules is described by Kwok, P. Y. et al. This method, which is an extension of PCR-based screening procedures uses an ELISA-based oligonucleotide-ligation assay (OLA) to detect the PCR products that contain the target source (Kwok, P. Y. et al., *Genomics* 13: 935–941 (1992)). The OLA employs an "reporter probe" and a phosphorylated/biotinylated "anchor" probe, which is captured with immobilized streptavidin (Landegren, U. et al., *Science* 241:1077–1080 (1988)).

The isolation of target DNA from a complex population using a subtractive hybridization technique has also been described (Lamar, E. E. et al., *Cell* 37:171–177 (1984); Rubenstein, J. L. R. et al., *Nucleic Acids Res.* 18:4833–4842 (1990); Hedrik, S. M. et al., *Science* 308:149–153 (1984); Duguid, J. R. et al., *Proc. Natl. Acad. Sci. (U.S.A.)* 85:5738–5742 (1988)). In such "subtractive hybridization" screening methods, the cDNA molecules created from a first population of cells is hybridized to cDNA or RNA of a second population of cells in order to "subtract out" those cDNA molecules that are complementary to nucleic acid molecules present in the second population and thus reflect nucleic acid molecules present in both populations The method is illustrated by Duguid, J. R. et al. (*Proc. Natl. Acad. Sci. (U.S.A.)* 85:5738–5742 (1988)) who used subtractive hybridization to identify gene sequences that were expressed in brain tissue as a result of scrapie infection. A cDNA preparation made from uninfected cells was biotinylated and permitted to hybridize with cDNA made from infected cells in a sample. Sequences in common hybridized to one another, and were removed from the sample through the use of a biotin-binding (avidin) resin.

Weiland, I. et al. (*Proc. Natl. Acad. Sci. (U.S.A.)* 87:2720–2724 (1990)) reported an improved method of subtractive hybridization in which tester DNA was cleaved with a restriction endonuclease, and then permitted to hybridize to sheared driver DNA at high $c_0t$ values ("$c_0t$" is the product of the initial concentration of DNA and the time of incubation). By cloning the double-stranded, PCR-amplified, unique DNA molecules into a plasmid vector, it was possible to obtain an enrichment in the relative proportion of target sequences recovered.

Rubenstein, J. L. R. et al. (*Nucleic Acids Res.* 18:4833–4842 (1990)) reported a further improvement in subtractive hybridization methods that employed single-stranded phagemid vectors to provide both the target and tester DNA. In the method, hybridized phagemid DNA-biotinylated driver strand complexes are separated from unhybridized DNA by the addition of streptavidin. Unhybridized single-stranded DNA was subsequently converted to the double-stranded form using Taq DNA polymerase and an oligonucleotide complementary to a common region found within the single-stranded DNA. The use of this method is, however, limited by the need to follow a rigorous single-stranded phagemid purification protocol in order to obtain a preparation virtually free of contaminant double-stranded DNA. (Rubenstein, J. L. R. et al., *Nucleic Acids Res.* 18: 4833–4841 (1990)).

In sum, methods for isolating particular target nucleic acid molecules are restricted by the abundance of the DNA target sequence, and by time-consuming steps. Accordingly, a method that would expedite the isolation of desired target nucleic acid molecules and that could yield essentially pure target DNA would be highly desirable.

SUMMARY OF THE INVENTION

The present invention provides a method for rapidly isolating nucleic acid molecules having a desired nucleotide sequence from other undesired nucleic acid molecules. Significantly, the present invention further relates to an improved method of screening target nucleic acid molecules employing hybridization methodology combined with ligand separation, DNA repair, and restriction enzyme digestion technology.

In detail, the invention provides a method for recovering a desired target nucleic acid molecule from a sample containing a mixture or library of single-stranded nucleic acid containing the molecule, wherein the method comprises the steps:

A. incubating the sample containing the nucleic acid mixture or library in the presence of a primer nucleic acid molecule complementary to a sequence of the desired target molecule; the incubation being under conditions sufficient to permit the template-dependent extension of the primer to thereby generate a double-stranded desired target molecule;

B. transforming single-stranded and double-stranded members of the mixture or library into a host cell, and C. recovering the desired molecule from the cell.

The invention additionally provides the embodiment wherein prior to commencing step A, the method comprises the presteps:

(1) incubating an initial sample containing the nucleic acid mixture or library in the presence of a haptenylated nucleic acid probe molecule, the probe molecules having a sequence complementary to a nucleotide sequence of the desired target molecule; the incubation being under conditions sufficient to permit the probe to hybridize to the desired target molecule and to thereby generate a hybridized molecule wherein the target molecule is bound to the probe;

(2) incubating the sample containing the nucleic acid mixture or library and biotinylated probe-target hybridized molecules of prestep (1) in the presence of a binding ligand of the hapten of the haptenylated probe, the binding ligand being conjugated to support; the incubation being sufficient to permit the probe molecules, and the probe-target hybridized molecule to become bound to the binding ligand of the support;

(3) recovering the probe-target hybridized molecules bound to the support from the nucleic acid mixture or library and any unbound biotinylated probe-target hybridized molecules of prestep (2); and (4) incubating the recovered support containing the bound probe-target hybridized molecules under conditions sufficient to separate the strands of double-stranded molecules; the incubation thereby releasing the hybridized target molecule from the biotinylated probe, and generating a sample single-stranded desired target molecule for use in step (A).

The invention additionally provides the embodiment wherein the single-stranded nucleic acid molecule of the sample contains a nucleotide analog, and wherein after completing step A, but prior to commencing step B, the method additionally comprises the presteps:

(1') incubating the generated double-stranded molecules in the presence of a nuclease capable of degrading nucleic acid containing nucleotide analog residues; and (2') incubating non-degraded nucleic acid with a primer under conditions sufficient to permit the primer to be extended in a template-dependent manner.

The invention additionally provides the embodiment wherein in step A, the template-dependent extension of the primer is conducted in the presence of a nuclease resistant nucleotide analog to thereby generate a double-stranded desired target molecule containing a residue of the nucleotide analog; and wherein prior to commencing the step B, the method additionally comprises the presteps:

(1") incubating the generated double-stranded desired target molecule in the presence of a nuclease, wherein the nuclease is substantially unable to cleave a nucleic acid molecule containing the nucleotide analog residue, but is substantially capable of degrading both single-stranded nucleic acid molecules and double-stranded nucleic acid molecules that lack the nucleic acid analog residue; the incubation being under conditions sufficient to permit such degradation, and thereby substantially eliminating both single-stranded nucleic acid molecules and double-stranded nucleic acid molecules that lack the nucleic acid analog residue from the sample; and thereby forming a preparation having a substantial enrichment of the desired target molecule relative to the initial sample; and (2") recovering the desired molecule from the preparation of prestep (1") to thereby form a library or mixture for the step B. The invention particularly concerns the embodiments of the above methods wherein the desired target nucleic acid molecule is a DNA molecule, a single-stranded nucleic acid molecule, a circular nucleic acid molecule and most preferably, a single-stranded, circular DNA molecule.

The invention particularly concerns the embodiments of the above methods wherein the desired target nucleic acid molecule is a DNA or RNA molecule, a single-stranded nucleic acid molecule, a circular nucleic acid molecule and most preferably, a single-stranded, circular DNA molecule.

The invention also concerns the embodiments of the above methods wherein the hapten is biotin, and wherein the binding ligand of the hapten is avidin, streptavidin, or antibody or antibody fragments that bind biotin.

The invention also concerns the embodiments of the above methods wherein the support is a bead, especially a paramagnetic bead that can be recovered by magnetic means or other physical separation.

The invention also concerns the embodiments of the above methods wherein the sequence of the primer molecule may be complementary to the same sequence of the desired target molecule as the probe molecule, or it may be complementary to a different sequence.

DESCRIPTION OF THE PREFERRED EMBODIMENTS

Figure 1:
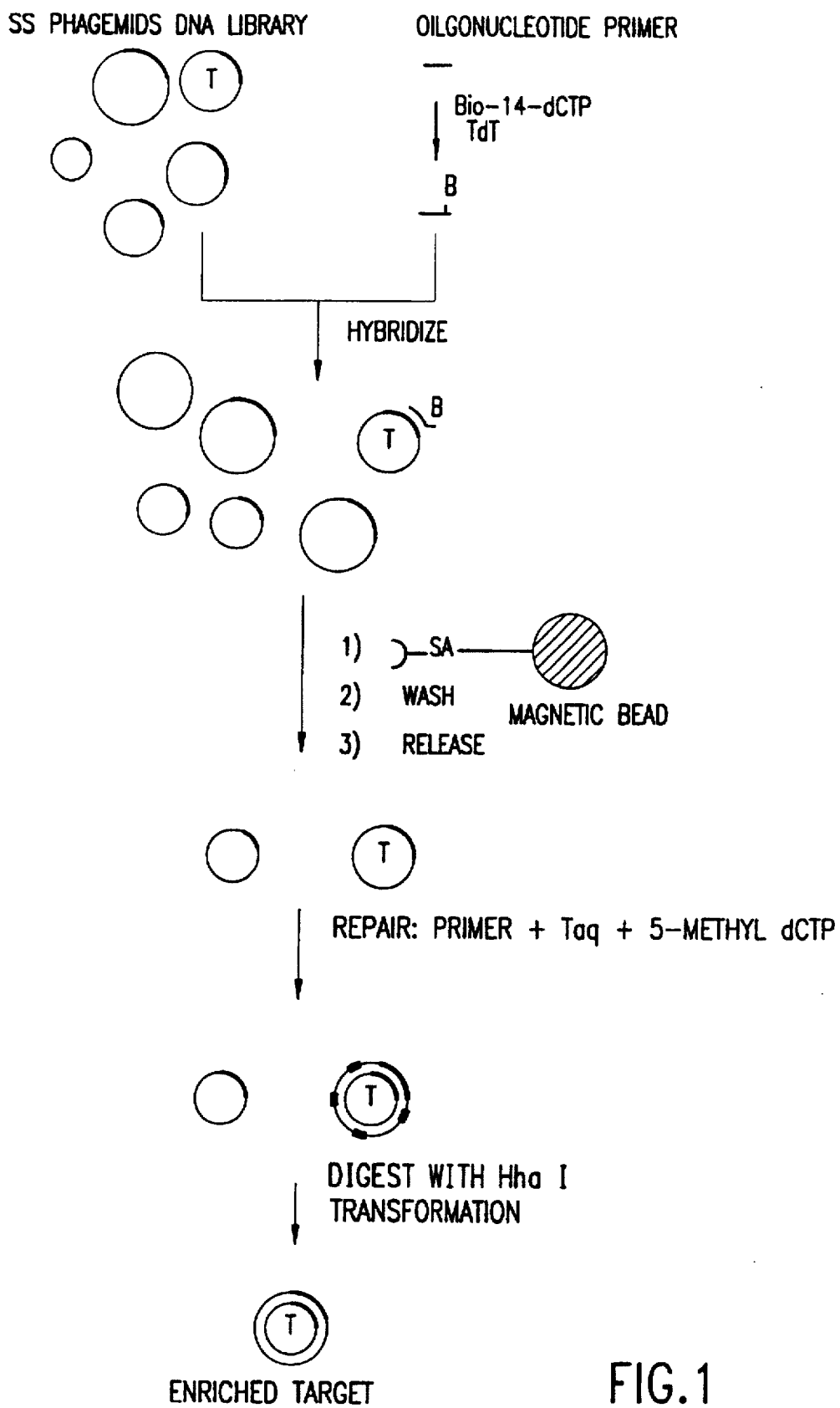
FIG. 1 provides a diagrammatic illustration of a preferred embodiment of the isolation method of the present invention.

The present invention concerns an improved method for rapidly isolating a "desired" nucleic acid "clone" from a mixture or library of cloned molecules. The "clones" of the present invention comprise circular or linear DNA or RNA molecules that may be either single-stranded or double-stranded. Typically, such clones or libraries will comprise plasmids or other vectors (such as viral vectors) that have been engineered to contain a fragment of DNA or RNA derived from a source such as a homogeneous specimen (such as cells in tissue culture, cells of the same tissue, etc.), or a heterogeneous specimen (such as a mixture of pathogen-free and pathogen-infected cells, a mixture of cells of different tissues, species, or cells of the same or different tissue at different temporal or developmental stages, etc.). The cells, if any, of these nucleic acid sources may be either prokaryotic or eukaryotic cells (such as those of animals, humans and higher plants).

Various libraries can be selected for large scale preparation. The construction of plasmid, cosmid, and phagemid cDNA libraries, or genomic libraries are described in Sambrook, J. et al., In: *Molecular Cloning, A Laboratory Manual*, 2nd Ed., Cold Spring Harbor Laboratory Press, Cold Spring Harbor, N.Y. (1989)). Preferably, single-stranded phagemid cDNA libraries can be prepared as described previously by Gruber, C. E. et al., *Focus* 15: (1993)). The general steps of the method will differ depending upon whether the desired sequence has been cloned into single-stranded or double-stranded molecules, and whether such molecules are DNA or RNA.

As used herein, there is no constraint as to the sequence of the target nucleic acid molecule whose isolation is desired. Since the present invention relies upon nucleic acid hybridization, the target molecule should have a length of at least 10 nucleotides in order to be efficiently recovered. No upper limit to the size of the molecules exists, and the methods of the invention can be used to isolate nucleic acid molecules of several kilobases or more.

The selection method of the present invention is based in part upon the observation that double-stranded nucleic acid molecules transform bacterial cells with greater efficiency than single-stranded nucleic acid molecules. In one embodiment, the invention achieves the isolation of a desired nucleic acid sequence from a library of sequences by providing a primer molecule to the mixture. A "primer" or "primer molecule" as used herein is a single-stranded oligonucleotide or a single-stranded polynucleotide that can be extended by the covalent addition of nucleotide monomers during the template-dependent polymerization reaction catalyzed by a polymerase. A primer is typically 11 bases or longer; most preferably, a primer is 17 bases or longer. Examples of suitable DNA polymerases include the large proteolytic fragment of the DNA polymerase I of the bacterium *E. coli*, commonly known as "Klenow" polymerase, *E. coli* DNA polymerase I, the bacteriophage T7 DNA polymerase. Preferably, a thermostable polymerase will be used, such as a polymerase that can catalyze nucleotide addition at temperatures of between about 50° C. to about 100° C. Exemplary thermostable polymerases are described in European Patent Appln. 0258017, incorporated herein by reference. The thermostable "Taq" DNA polymerase (Life Technologies, Inc., Gaithersburg, Md.) is particularly preferred.

Where the target mixture involved RNA molecules, and a DNA molecule is desired, a reverse transcriptase may be employed. Reverse transcriptases are discussed by Sambrook, J. et al. (In: *Molecular Cloning: A Laboratory Manual*, Cold Spring Harbor Laboratory Press, Cold Spring Harbor, N.Y. (1989)) and by Noonan, K. F. et al. (*Nucleic Acids Res.* 16:10366 (1988)). Similarly, where the target mixture involved RNA, an RNA polymerase may be used. Examples of suitable RNA polymerases include *E. coli* RNA polymerase, T7 RNA polymerase, etc.

As a consequence of such polymerization, the desired target molecule, but not other nucleic acid molecules of the mixture, is converted into a double-stranded form. The mixture can, without further processing, be transformed into suitable recipient bacteria (see, Sambrook, J. et al., In: *Molecular Cloning: A Laboratory Manual*, Cold Spring Harbor Laboratory Press, Cold Spring Harbor, N.Y. (1989)). Transformants can be recovered, and their recombinant DNA or RNA molecules can be extracted and retrieved. Such processing provides a new mixture or library of nucleic acid molecules that is substantially enriched for the desired molecule. Optionally, the above-described method can be repeated (as often as desired) in order to obtain mixtures or libraries that are more highly enriched for the desired nucleic acid sequence.

A preferred method for conducting such processing employs a library or mixture of a single-stranded phagemid, such as M13. In such a method, a primer is used to convert the single-stranded DNA molecule into a double-stranded form.

A. Capture Enrichment of Desired Molecules

In a first preferred embodiment, the selection method of the present invention can be augmented through the use of an optional nucleic acid "capture" step. This embodiment is preferably performed using single-stranded nucleic acid molecules. Where double-stranded circular molecules are employed, a preferred initial step involves denaturing the molecules into their respective single strands. Most preferably, this is accomplished by transient incubation of the sample at elevated temperatures (60°–80° C. or above the $T_m$ of the mixture). Alternatively, salt or ionic conditions can be adjusted, or denaturation can be accomplished via helicase activity. The strand-separation step may require a topoisomerase in order to permit full strand separation. Alternatively, the double-stranded plasmid or linear target DNA could be nicked and the nicked strand removed by denaturation or digestion. In addition, double-stranded linear DNA could be denatured or one strand digested. These methods would leave one strand of DNA intact for hybrid selection.

In accordance with the invention, such a population of single-stranded molecules is then incubated in the presence of an oligonucleotide probe under conditions sufficient to permit and promote sequence-specific nucleic acid hybridization. Hybridization may be conducted under conditions which either permit or minimize random hybridization. As used herein, conditions which minimize random hybridization are of such stringency that they permit hybridization only of sequences that exhibit complete complementarity. In contrast, conditions that permit random hybridization will enable molecules having only partial complementarity to stably hybridize with one another. Suitable conditions which either permit or minimize random nucleic acid hybridization are described by Maniatis, T., et al. (In: *Molecular Cloning, A Laboratory Manual,* Cold Spring Harbor Laboratories, Cold Spring Harbor, N.Y. (1982)), by Haymes, B. D., et al. (In: *Nucleic Acid Hybridization, A Practical Approach,* IRL Press, Washington, DC (1985), herein incorporated by reference), and similar texts.

The probe is a nucleic acid molecule, preferably DNA, preferably greater than 8–12 nucleotides in length, and most preferably greater than 15–30 nucleotides in length, whose sequence is selected to be complementary to the sequence of a region of the target molecule that is to be isolated. The probe thus need not be, and most preferably will not be equal in size to the target molecule that is to be recovered. Two sequences are said to be "complementary" to one another if they are capable of hybridizing to one another to form a stable anti-parallel, double-stranded nucleic acid structure. Thus, the sequences need not exhibit precise complementarity, but need only be sufficiently complementary in sequence to be able to form a stable double-stranded structure. Thus, departures from complete complementarity are permissible, so long as such departures are not sufficient to completely preclude hybridization to form a double-stranded structure.

In some embodiments, the sequence of the probe and/or the primer may be derived from amino acid sequence data. In these instances, the probe and/or the primer may have a degenerate sequence. For instance, if one had an amino acid motif (e.g. zinc fingers) that occurred in a number of proteins encoded in a library, one could enrich for nucleic acids encoding proteins having that motif.

In a preferred sub-embodiment, the probe is "haptenylated." As used herein, a "haptenylated" probe is a nucleic acid molecule that has been covalently bonded to a hapten molecule. A hapten is a molecule that can be recognized and bound by another molecule, e.g. an antibody. Examples of haptens include any antigen, biotin, dinitrophenol, etc. Biotin is a preferred hapten of the present invention and may be bound by proteins such as avidin and streptavidin. The probe may be "haptenylated" using any of a variety of methods well known in the art. For example, methods for "biotinylating" the probe are described, for example, by Hevey et al. (U.S. Pat. No. 4,228,237); Kourilsky et al. (U.S. Pat. No. 4,581,333); Hofman et al. (*J. Amer. Chem. Soc.* 100:3585–3590 (1978)); Holmstrom, K. et al. (*Anal. Biochem.* 20:278–283 (1993)), etc. Such modification is most preferably accomplished by incorporating biotinylated nucleotides into a nucleic acid molecule using conventional methods. Alternatively, such modification can be made using photobiotin (Vector Laboratories). Other methods can, of course, be employed to produce such biotinylated molecules.

The above-described incubation thus results in the hybridization of the biotinylated probe and the desired target sequence such that a double-stranded region is formed. In the next step of the preferred method, this complex is "captured" using a an immobilizable support, most preferably, a paramagnetic bead. In a preferred sub-embodiment, the capture of the hybridized biotinylated probe is initiated without the necessity for removing non-hybridized molecules.

The support is modified so as to have a binding ligand of biotin conjugated to it. Suitable binding ligands include avidin, or streptavidin, or antibody or antibody fragments that bind biotin. Methods for effecting such covalent attachment are described by Hevey et al. (U.S. Pat. No. 4,228,237) and by Kourilsky et al. (U.S. Pat. No. 4,581,333). Suitable solid supports include, but are not limited to, beads, tubes, or plates, which may be made of materials including, but not limited to, latex, glass, polystyrene, polypropylene or other plastic. Such supports can be 2-dimensional strips, beads, etc. A preferred support is a paramagnetic-streptavidin conjugated bead, such as the Dynabead Streptavidin M-280 bead (Dynal, Great Neck, N.Y.).

The addition of the beads (or other support) to the reaction permits the biotinylated probe to bind to the avidin (or other biotin ligand) of the beads. Such binding reactions are very strong. For example, the binding constant for the reaction between avidin and biotin is approximately $10^{15}$ 1/mole. The very strong nature of this bond has been found to persist even when biotin is conjugated, by means of its carboxyl group, to another molecule, or when avidin is attached to another molecule.

As a consequence of such binding, any biotinylated probe that has hybridized to a desired target molecule will become bound to the bead or support. In contrast, non-target molecules will remain unbound, and can be separated from the bound material by washing, filtration, centrifugation, sieving, or by magnetic separation methods. Most preferably, however, a magnet is used to pull the paramagnetic bead out of solution, and the beads are washed with a suitable buffer (such as one containing Tris, EDTA, and NaCl). Such treatment removes the majority of non-target nucleic acid sequences that were originally present, and hence eliminates undesired non-selected single-stranded phagemid DNA from the reaction.

The specifically captured single-stranded phagemid target DNA (hybridized to the biotinylated probe) is then released from the probe by treatment such as addition of an alkaline buffer, heat, etc. In a preferred sub-embodiment, the selected target DNA is resuspended in a formamide-Tris-EDTA buffer and released from the beads by heating at a temperature of 60°–70° C. for a short period of time. The releasing treatment is preferably selected such that the biotinylated probe remains attached to the magnetic beads, which is then removed from solution by sieving, centrifugation, filtration, or more preferably, by a magnet.

B. Nuclease Enrichment of Desired Molecules

In a second preferred embodiment, a nuclease enrichment protocol can optionally be used to aid, or further aid in effecting the isolation of a desired target DNA molecule. Where employed, the second embodiment can either be used alone, or in conjunction with the above-described first preferred embodiment.

As in the case of the first preferred embodiment, single-stranded nucleic acid is desired. Thus, where double-stranded nucleic acid is employed, any of the above-described methods can be used to obtain a suitable single-stranded molecule. Such single-stranded molecules are converted to their double-stranded DNA form using a DNA polymerase and in the presence of requisite nucleotide triphosphates, and factors, and an oligonucleotide primer. Where the first and second embodiments are to be performed in conjunction, the primer employed in the second embodiment may comprise all or a subset of the sequence present in the haptenylated probe molecule of the first embodiment. In such a sub-embodiment, therefore, the conversion step need not further sort or distinguish among the recovered molecules. Preferably, stringent hybridization conditions are used and the conversion step is done at high temperature with a thermostable polymerase, e.g. Taq polymerase. In this case, because the hybridization and conversion are done under conditions favorable to correct hybrids, the conversion step does further enrich or select for the desired target molecule. In an alternative sub-embodiment, the primer molecule may comprise a sequence that although present on the desired target molecule was not contained on the "haptenylated" probe. Such a sub-embodiment permits the experimentalist to purify only a subset of the initially present molecules. For example, if the probe was designed to hybridize to any member of a gene library that had a particular enhancer sequence, and the primer were designed to hybridize only to a receptor binding site, the net effect of the reaction would be to obtain double-stranded molecules that contained both the enhancer sequence and the receptor binding site.

Note that the hapten need not be covalently coupled to the probe-nucleic acid. The hapten may be linked, either covalently or non-covalently, to a molecule that non-covalently binds the probe molecule, e.g. a single-stranded DNA binding protein. The binding protein must bind tightly enough that significant quantities of it will not fall off of the probe molecules and bind to nucleic acid molecules of the sample.

The template-dependent extension of the primer is conducted in the presence of at least "nucleotide analog" (either in lieu of or in addition to the naturally occurring analog). A "nucleotide analog," as used herein, refers to a nucleotide which is not found in the target DNA or RNA that is the primer's template. For example, where the isolated target molecule is DNA, suitable nucleotide analogs include ribonucleotides, deoxyuridine, bromodeoxyuridine, 7-methylguanine, 5-methyldeoxcytosine, 5,6-dihyro-5,6-dihydroxydeoxythymidine, 3-methyldeoxyadenosine, etc. (see, Duncan, B. K., *The Enzymes XIV*:565–586 (1981)). Other nucleotide analogs will be evident to those in the art. Where the template is RNA, deoxynucleotide triphosphates and their analogs are the preferred nucleotide analogs. Any single-stranded non-target DNA that remains after the conversion step may contribute a background of non-target sequences in molecules recovered by the present method, therefore, it is desirable to remove or eliminate any single-stranded DNA that might remain.

The presence of the nucleotide analog in the reaction will result in the production of a double-stranded molecule that contains incorporated analog bases. Such incorporation affects the ability of endonucleases and exonucleases to cleave or degrade the double-stranded molecule. Thus, in a particularly preferred sub-embodiment, a primer is extended from a circular DNA template in the presence of a methylated nucleotide (for example, 5-methyl dCTP). The resulting double-stranded molecule, which contains incorporated 5-methyl C residues, is resistant to cleavage by many restriction endonucleases. HhaI is particularly preferred when used in conjunction with 5-methyl C, since it also degrades single-stranded DNA, the effect of incubation in the presence of such enzymes is to destroy most or all residual undesired non-target molecules present, and to thereby greatly enrich the concentration of the desired vector. Other nucleotide analogs that inhibit or block exonucleases or restriction endonucleases are 6-methyladenine, 5-methylguanine and 5-methylcytidine. Combinations of nucleotide analogs and suitable enzymes are known in the art (see, for example, Life Technologies™ 1993–1994 Catalogue and Reference Guide, Chapter 6, Life Technologies, Inc., Gaithersburg, Md., herein incorporated by reference).

In a similar manner, where the source library was composed of single-stranded RNA vectors, the use of dNTPs (i.e. dATP, dTTP, dCTP, and dGTP) in the conversion step will render such molecules resistant to mung bean nuclease, or Bal-31 nuclease.

Although the foregoing discussion has emphasized the use of circular molecules, the methods of the present invention are fully amenable to the use of linear molecules. In such a case, the primer molecule (but not necessarily the probe molecule) is preferably selected such that it hybridizes to the 5' terminus of the target molecule. Such selection will permit the template-dependent extension of the molecule to produce a full length copy of the target molecule.

Desirably, the recovered target DNA is then precipitated with organic solvents, and resuspended in buffer. The product may then be transfected or electroporated into recipient cells, for example by the method of Rubenstein et al. (*Nucl Acids Res.* 18: 4833 (1990), herein incorporated by reference).

Having now generally described the invention, the same will be more readily understood through reference to the following examples which are provided by way of illustration, and are not intended to be limiting of the present invention, unless specified.

EXAMPLE 1

Preferred Method for Isolating Desired Target Molecules

A preferred method for isolating a desired target molecule employs a library or mixture of a single-stranded phagemid, such as M13. In such a method, the single-stranded phagemid is introduced into an ung dut mutant of *E. coli* (Kunkel, T. A., U.S. Pat. No. 4,873,192; Longo, M. C. et al., *Gene* 93:125–128 (1990); Hartley, U.S. Pat. No. 5,035,966; all herein incorporated by reference). The "+" strand of phagemids grown in such mutants contains deoxyuridine (dUTP), and can be recovered from the packaged virion. Thus, the use of such mutants permits the isolation of a library or mixture that comprises single-stranded DNA molecules which contain dU residues (Kunkel, T. A., U.S. Pat. No. 4,873,192).

The recovered DNA can then be optionally captured via a capture step, or directly processed using a nuclease enrichment step.

If a capture step is to be conducted, the dU-containing strands are incubated in the presence of a complementary biotinylated probe. The probe, and any hybridized DNA is then recovered by permitting the biotin to bind to avidin-coated paramagnetic beads, and then recovering the beads from solution using a magnet. The library or mixture is recovered from the beads by denaturation of the hybridized molecules.

The recovered single-stranded DNA is then incubated in the presence of a complementary primer, dATP, dTTP, dCTP, and dGTP and under conditions sufficient to permit the extension of the primer. Such extension thus creates a sample that contains single-stranded dU-containing molecules and double-stranded dU/dT hybrid (desired target) molecules.

Although the triphosphate form of deoxyuridine, dUTP, is present in living organisms as a metabolic intermediate, it is rarely incorporated into DNA. When dUTP is incorporated into DNA, the resulting deoxyuridine can be promptly removed in vivo by the enzyme uracil DNA glycosylase (UDG) (Kunkel, U.S. Pat. No. 4,873,192; Duncan, B. K., *The Enzymes XIV*:565–586 (1981), both references herein incorporated by reference in their entirety).

In this embodiment of the present invention, the mixture of molecules is then treated, either in vivo or in vitro with UDG. Such treatment destroys all of the single-stranded, non-desired, non-target molecules in the sample. It further destroys the "+" strand of all of the double-stranded desired target molecules.

The sample is therefore then either directly transformed into *E. coli* to permit the isolation of the target molecule or incubated in the presence of a primer molecule that is capable of hybridizing to the "−" strand of the phagemid. Such incubation is under conditions suitable for mediating the template-dependent extension of the primer. Hence, such incubation produces double-stranded molecules that have the sequence of the desired target molecules, and thereby permit the isolation of the target molecule.

EXAMPLE 2

Preparation of Single-stranded DNA

The large scale preparation of single-stranded phagemid cDNA library was made as described previously (Gruber, C. E. et al., *Focus* 15 (1993), herein incorporated by reference).

Preparation of Biotinylated Oligonucleotides

The oligonucleotide probes were biotin-labeled using biotin-14-dCTP and terminal deoxynucleotidyl transferase (TdT) as described by Flickinger, J. L. et al. (*Nucl. Acids Res.* 20: 2382 (1992)) with the following minor modifications. In a typical reaction, 0.3–0.5 nmol ($\approx$5 µg) of oligonucleotides (21-25-mer), 500 µM of biotin-14-dCTP and 60 units of TdT in 50 µl of 1× tailing buffer [100 mM potassium cacodylate (pH 7.2), 2 mM $CoCl_2$ and 200 µM DTT] was incubated at 37° C. for 15 min. The reaction was terminated by adding 2 µl of 0.25M EDTA. The labeled probes were precipitated by adding an equal volume (52 µl) of 1M Tris buffer (pH 7.5), 10 µg glycogen as carrier, and 2.5 volume (260 µl) of ethanol, and stored on dry ice for 10 min. After centrifugation at 4° C. for 10 min, the probes were rinsed with 100 µl of 75% ethanol and centrifuged for 2 min. The probes were air-dried and dissolved in 10 µl of TE. To determine the labeling efficiency and the concentration of the labeled probe, 2 µl of labeled products were resuspended in an equal volume of sequencing reaction stop buffer [95% (v/v) formamide, 10 mM EDTA (pH 8.0), 0.1% (w/v) bromophenol blue, 0.1% (w/v) xylene cyanol], heated at 95° C. for 1 min and chilled on ice. The probes were electrophoresed along with a known amount of the starting material on 16% denaturing PAGE. The gel was soaked in a ethidium bromide solution (0.5 µg/ml) for 15 min, and photographed. Typically, more than 95% of the oligonucleotide will be labeled. The concentration of the labeled probes was determined by the comparison to the known starting material.

Hybrid Selection

The hybridization was performed by the following procedure: 1–10 µg of single-stranded target library DNA was diluted with 10 µl of dilution buffer (100 mM HEPES, pH 7.5, 2 mM EDTA and 0.2% SDS) to a final volume of 19 µl in a 5 ml Falcon tube. The DNA was denatured at 95° C. for 1 min and immediately chilled in ice water for 5 min. 1 µl (20 ng) of biotin-probe was added to the DNA mixture, followed by the addition of 5 µl of 5M NaCl. The hybridization mixture was incubated at 42° C. with continuous shaking (200 rpm) in a culture incubator for 24 h. Before binding the hybrids to the streptavidin, 50 µl of the streptavidin coated paramagnetic beads (DYNAL) were washed once with 1× binding buffer (10 mM TRIS, pH 7.5, 1 mM EDTA and 1M NaCl) by following the manufacturer's instructions. The paramagnetic beads were resuspended in 20 µl of 1× binding buffer. The hybridization mixture was added to the resuspended beads and mixed well. The mixture was incubated at room temperature for 1 h with occasional mixing by gently tipping the tube. The paramagnetic beads were separated from the DNA bulk by inserting the tube into the magnet, and washed 6 times with the washing buffer (10 mM Tris, pH 7.5, 1 mM EDTA and 500 mM NaCl). Finally, the paramagnetic beads were resuspended in 20 µl of 30% formamide in TE buffer. The selected DNA was released by heating the beads at 65° C. for 5 min. The tube was inserted into the magnet, and the aqueous phase was transferred to a new tube. The beads were washed once with 15 µl of TE buffer, and the aqueous phases were pooled. The selected DNA was precipitated with 0.5 volumes of 7.5M ammonium acetate, 10 µg of glycogen, and 2.5 volume of ethanol. The DNA pellet was dissolved in 5–10 µl of TE buffer. An aliquot (1 µl) was used for the electroporation to determine the hybrid selection efficiency.

Repair of Single-Stranded DNA

The remainder of the selected single-stranded DNA was converted to double-stranded DNA before electroporation as described by Rubenstein et al. (*Nucl. Acids Res.* 18: 4833 (1990)) with some modifications. The reaction was carried out in 30 µl containing the selected single-stranded DNA, 250 ng of unlabeled primer, 300 µM each dTTP, dGTP, dATP and 5-methyl dCTP, Taq DNA polymerase buffer and 2 units of Taq DNA polymerase. After repair, the mixture was extracted once with phenol:chloroform. The organic phase was back-extracted with 15 µl of TE, the aqueous phases were pooled and ethanol precipitated. The pellet was rinsed with 100 µl of 75% ethanol and dried. The repaired DNA was dissolved in 5–10 µl of TE and digested with HhaI for 2 h at 37° C. After digestion, the mixture was extracted once with phenol:chloroform, ethanol precipitated and dissolved in 5–10 µl of TE.

Detection of the Target Gene

The repaired, digested DNA was used to transform *E. coli* bacteria (DH10B background) by chemical transformation or electroporation. The target colony can be detected by the PCR, colony hybridization or cycle sequencing approach.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for recovering a desired target nucleic acid molecule from an initial mixture or library of nucleic acid molecules containing said molecule, wherein said method comprises the steps:

(A) (1) where said initial mixture or library is composed of single-stranded nucleic acid molecules, performing step (B); or (2) where said initial mixture or library is composed of double-stranded nucleic acid molecules treating said double-stranded nucleic acid molecules to render such molecules single-stranded, then performing step (B);

(B) incubating the single-stranded nucleic acid molecules of said mixture or library in the presence of a haptenylated nucleic acid probe molecule, said probe molecule comprising a unique nucleotide sequence complementary to a nucleotide sequence of said desired target molecule; said incubation being under conditions sufficient to permit said probe to hybridize to said desired target molecule and to thereby generate a hybridized molecule wherein said desired target molecule is bound to said probe;

(C) capturing said hybridized molecule of step (B) by incubating said hybridized molecule in the presence of a binding ligand of the hapten of said haptenylated probe, said binding ligand being conjugated to a support; said incubation being sufficient to permit said hybridized molecule to become bound to said binding ligand of said support;

(D) separating said bound hybridized desired target molecule from unbound nucleic acid molecules; and (E) recovering said desired target molecule from said support.

2. The method of claim 1, wherein in step (B), said desired incubation is under conditions which minimize random hybridization.

3. The method of claim 1, wherein said desired target nucleic acid molecule is a DNA molecule.

4. The method of claim 3, wherein said initial mixture or library is composed of single-stranded DNA.

5. The method of claim 4, wherein said single-stranded DNA is circular.

6. The method of claim 4, wherein said single-stranded DNA is linear.

7. The method of claim 4, wherein the single-stranded DNA of said initial mixture or library is selected from the group consisting of single-stranded plasmids, single-stranded cosmids and single-stranded phagemids.

8. The method of claim 7, wherein the single-stranded DNA of said initial mixture or library are single-stranded plasmids.

9. The method of claim 7, wherein the single-stranded DNA of said initial mixture or library are single-stranded cosmids.

10. The method of claim 7, wherein the single-stranded DNA of said initial mixture or library are single-stranded phagemids.

11. The method of claim 3, wherein said initial mixture or library is composed of double-stranded DNA molecule.

12. The method of claim 11, wherein said double-stranded DNA is circular.

13. The method of claim 11, wherein said double-stranded DNA is linear.

14. The method of claim 11, wherein the double-stranded DNA of said initial mixture or library is selected from the group consisting of double-stranded plasmids, double-stranded cosmids and double-stranded phagemids.

15. The method of claim 14, wherein the double-stranded DNA of said initial mixture or library are double-stranded plasmids.

16. The method of claim 14, wherein the double-stranded DNA of said initial mixture or library are double-stranded cosmids.

17. The method of claim 14, wherein the double-stranded DNA of said initial mixture or library are double-stranded phagemids.

18. The method of claim 14, wherein said mixture or library of double-stranded DNA is nicked prior to said treatment of step (A)(2).

19. The method of claim 18, wherein said treatment step comprises degradation of one strand of said double stranded DNA.

20. The method of claim 1, wherein said hapten is biotin.

21. A method according to claim 20, wherein a biotin molecule is covalently bonded to the 3' terminus of said probe.

22. The method of claim 20, wherein said binding ligand of said biotin is selected from the group consisting of avidin, streptavidin, an antibody that binds biotin and an antibody fragment that binds biotin.

23. The method of claim 22, wherein said binding ligand of biotin is avidin.

24. The method of claim 22, wherein said binding ligand of biotin is streptavidin.

25. The method of claim 22, wherein said binding ligand of biotin is an antibody that binds biotin.

26. The method of claim 22, wherein said binding ligand of biotin is an antibody fragment that binds biotin.

27. The method of claim 1, wherein said separating step (D) is accomplished by magnetic means.

28. The method of claim 27, wherein said support is a paramagnetic bead.

29. The method of claim 1, which additionally includes the step:

(F) incubating said single-stranded desired target molecule of step (E) in the presence of a primer nucleic acid molecule complementary thereto; said incubation being under conditions sufficient to permit hybridization between said primer and said desired target molecule, and further sufficient to permit the template-dependent extension of said primer to thereby generate a nucleic acid molecule complementary to said desired target molecule.

30. The method of claim 29, wherein said primer molecule of step (F) is complementary to the same sequence of said desired target molecule as said probe molecule of step (B).

31. The method of claim 29, wherein in said primer molecule of step (F) is not complementary to the same sequence of said desired target molecule as said probe molecule of step (B).

32. The method of claim 29, wherein in step (B), said probe has a degenerate sequence.

33. The method of claim 29, wherein in step (F), said primer has a degenerate sequence.

34. The method of claim 29, wherein, in step (F), a second primer is additionally provided, said second primer being complementary to a sequence of said generated nucleic acid molecule that is complementary to said desired target molecule, and wherein step (F) is conducted under conditions sufficient to permit a selective amplification of said desired target molecule.

35. The method of claim 34, wherein said selective amplification is mediated by a polymerase chain reaction.

36. The method of claim 1, which additionally comprises the step of transforming the recovered desired target molecule of step (E) into a host cell.

37. The method of claim 29, wherein said step (F) generates a double-stranded nucleic acid molecule comprising said target molecule, and wherein said method additionally comprises the step:

(G) transforming said double-stranded desired target molecule of step (F) into a host cell.

38. The method of claim 35, which additionally comprises the step of transforming the amplified desired target molecule into a host cell.

39. The method of claim 37, wherein said double standard desired target molecule is selected from the group consisting of double stranded plasmids, double stranded cosmids and double stranded phagemids.

40. A method for recovering a desired target nucleic acid molecule from a sample comprising the steps:

(A) incubating said sample in the presence of a haptenylated nucleic acid probe molecule, said probe molecule comprising a unique nucleotide sequence complementary to said desired target molecule; said incubation being under conditions sufficient to permit said probe to hybridize to said desired target molecule and to thereby generate a hybridized molecule wherein the desired target molecule is bound to said probe;

(B) capturing said hybridized molecule of step (A) by incubating said hybridized molecule in the presence of a binding ligand of the hapten of said haptenylated probe, said binding ligand being conjugated to a support; said incubation being, sufficient to permit said hybridized molecule to become bound to said binding ligand of said support;

(C) separating said bound hybridized desired target molecule from unbound nucleic acid molecules;

(D) incubating said desired target molecule of step (C) in the presence of a primer nucleic molecule complementary to a sequence of the desired target molecule; said incubation being under conditions sufficient to generate a double stranded desired target molecule;

(E) releasing said double stranded target molecule from said solid support; and (F) transforming said double stranded desired target molecule of step (D) into a host cell.

41. The method of claim 40, wherein said double stranded desired target molecule is a DNA molecule which is selected from the group consisting of a plasmid, a cosmid, and a phagemid.

42. The method of claim 41, wherein said hapten is biotin and said binding ligand is selected from the group consisting of avidin, strepavidin, an antibody that binds biotin and an antibody fragment that binds biotin.

43. The method of claim 42, wherein said host cell is an *E. coli* cell.

44. The method of claim 43, wherein said transformation step is accomplished by chemical transformation or electroporation.

* * * * *